United States Patent [19]

O'Connor et al.

[11] Patent Number: 5,177,014

[45] Date of Patent: Jan. 5, 1993

[54] MONOCLONAL ANTIBODIES TO FELINE-T-LYMPHOTROPIC LENTIVIRUS

[75] Inventors: Thomas P. O'Connor, Westbrook; Quentin J. Tonelli; Philip R. Andersen, both or Portland, all of Me.

[73] Assignee: Idexx Laboratories, Inc., Westbrook, Me.

[21] Appl. No.: 446,008

[22] Filed: Dec. 5, 1989

Related U.S. Application Data

[63] Continuation-in-part of Ser. No. 293,906, Jan. 5, 1989, which is a continuation-in-part of Ser. No. 279,989, Dec. 5, 1988, abandoned.

[51] Int. Cl.⁵ ............................................... C12N 9/96
[52] U.S. Cl. ................................. 435/188; 530/388.5; 530/391.3; 435/5; 435/7.92
[58] Field of Search ............... 435/5, 7, 28, 172.2, 435/240.26, 240.27, 188; 436/536, 548, 813; 530/387, 389, 808, 809, 388.35

[56] References Cited

U.S. PATENT DOCUMENTS 4,514,505  4/1985  Canfield et al. .
5,037,753  8/1991  Pedersen et al. ................ 435/235.1

OTHER PUBLICATIONS

Yamamoto et al. (Am. J. Vet. Res. 49:1246, 1988).
Tilton et al. (J. Clin. Micro. 28:898, 1990).
Yamamoto et al. (Am. J. Vet. Res. 49:1246, 1988).
Tilton et al. (J. Clin. Micro. 28:898, 1990).
Lutz et al., J. Vet. Med. B35:773-778, 1988.
Sevier et al., Clin. Chem. 27:1797-1806, 1981.
Hellström et al., "Monoclonal Anti-melanoma Antibodies and Their Possible Clinical Use", Monoclonal Antibodies of Cancer Detection and Therapy; pp. 19-51 (1985).
Voller, "The Enzyme Linked Immunosorbent Assay (ELISA)", 2 Diagnostic Horizons; 1-7 (1978).
Pederson et al., "Isolation of a T-lymphotropic Virus From Domestic Cats With an Immunodeficiency-Like Syndrome", 235 Science 790, 1987.
O'Connor et al., "Characterization of the Major Structured Proteins of Feline T-Lymphotropic Lentivirus (FTLV)" J. Clin. Micro. P. 213, Mar. 1989.
Wilson et al., "Recent Developments in the Periodate Method Conjugating Horseradish Peroxidase," North Holland Biomedical Press, pp. 215-223 (1978).
Hardy "Feline T-Lymphotropic Lentivirus: Retrovirus-Induced Immunosuppression in Cats," Journal of the American Animal Hospital Assoc., pp. 241-243, vol. 25, 1988.
UC Clip Sheet (TRENDS) 1987.
Harbour et al., "Isolation of a T-lymphotropic Lentivirus From A persistently Leucopenic Domestic Cat," Veterinary Record, 122:84-86 (1988).
The Veterinary Record, "Implications of the Isolation of FTLV," vol. 122, No. 4, (1988).
Sparger, "Feline T-Lymphotrophic Lentivirus Infection," Feline Medicine IV; Veterinary Learning System, 1988 pp. 9-14.
Talbott et al., "Nucleotide Sequence and Genomic Organization of Feline Immunodeficiency Virus," 86 P.N.A.S. USA 5743-5747, Aug. 1989.
Olmsted et al. "Nucleotide Sequence Analysis of Feline Immunodeficiency virus; Genome Organization and Relationship to Other Lentiviruses," 86 P.N.A.S. (USA) 8088-8092 (Oct. 1989).

Primary Examiner—Esther L. Kepplinger
Assistant Examiner—Donna C. Wortman

[57] ABSTRACT

Monoclonal antibodies specific for an epitope of an FIV-encoded antigen.

11 Claims, 2 Drawing Sheets

5,177,014

MONOCLONAL ANTIBODIES TO FELINE-T-LYMPHOTROPIC LENTIVIRUS

BACKGROUND OF THE INVENTION

This application is a continuation-in-part of O'Connor et al., U.S. Ser. No. 293,906, filed Jan. 5, 1989, entitled "Monoclonal Antibodies To Feline-T-Lymphotropic Lentivirus,", which is in turn a continuation-in-part of O'Connor et al., U.S. Ser. No. 279,989, filed Dec. 5, 1988, entitled "Monoclonal Antibodies To Feline-T-Lymphotropic Lentivirus," abandoned, the whole of both of which (including drawings) are hereby incorporated by reference herein.

This invention relates to monoclonal antibodies to feline-T-lymphotropic lentivirus (also called feline immunodeficiency virus, FIV) and to use of these monoclonals for detection and purification of the virus.

Pedersen et al., 235 Science 790, 1987, describes detection and isolation of FIV from domestic cats having an immunodeficiency-like syndrome The virus was purified by centrifugation on sucrose gradients in Tris base pH 7.4 containing 0.1 M NaCl and 1 mM EDTA. Western blots prepared from gradient purified virus and their reaction with sera from experimentally infected cats was determined. A few protein bands were detected and "[a]lthough antigenic comparison was not made, the position of these bands may correspond to the major core protein p24, gag precursor protein p55 and endonuclease protein p32 of HIV".

Pedersen et al., U.S. Pat. No. 5,037,753 entitled FELINE T-LYMPHOTROPIC LENTIVIRUS (which is not admitted to be prior art to the present application) describes the results presented by Pedersen, supra, and states that Western blotting of FIV infected cell lysates yielded major bands at approximately 22–26 kD, usually about 24 kD; 50–60 kD, usually about 55 kD; and 28–36 kD, usually about 32 kD. They state that monoclonal antibodies may be prepared to FIV antigen by standard techniques, as described by Kohler and Milstein, 6 Eur. J. Immol 511, 1976.

SUMMARY OF THE INVENTION

In a first aspect, the invention features monoclonal antibodies specific for an epitope of an FIV-encoded antigen, e.g., a protein, polypeptide, or glycoprotein. By monoclonal antibody is meant any antibody that is produced from a single antibody-producing cell which has been cloned to produce an antibody-producing cell line. It does not include the various antibodies found in a polyclonal preparation, i.e., a preparation produced by inoculation of an animal with an antigen and recovery of the resulting serum. By epitope is meant any specific amino acid sequence, modified amino acid sequence, or protein secondary or tertiary structure which is recognized by an antibody. This epitope may be present on one or more antigens of FIV, but is not present in any of the other components commonly associated with FIV, for example, feline cells and serum.

In preferred embodiments, the epitope is present on an antigen selected from the group consisting of the p10, p15, p26, p47, p110, gp40 or gp130 antigens of FIV (i.e., those FIV-encoded antigens with molecular weights of 10, 15, 26, 40, 50, 110 or 130 kD as describe below); the antibody has sufficient affinity for the epitope to selectively identify the epitope in an immunoassay for FIV; the antibody recognizes an epitope on the FIV viral particle; the antibody is conjugated with a detectable label, the label not significantly interfering with the specificity or affinity of the antibody for the epitope, most preferably the label is an enzyme, e.g., horseradish peroxidase; and the antibody is produced by a cell line deposited with the American Type Culture Collection, and assigned the number HB9888, HB9889, or HB9890.

In a second aspect, the invention features a solution containing a plurality of the above monoclonal antibodies, each antibody being specific for an epitope gcf an FIV-encoded antigen.

In a third aspect, the invention features a method for detection of an epitope of an FIV-encoded antigen in a sample, including the steps of providing a monoclonal antibody specific for the epitope; contacting the antibody with the sample under conditions in which the antibody forms a complex with the epitope; and detecting the complex, wherein the presence of the complex indicates the presence of the epitope in the sample.

This invention provides monoclonal antibodies suitable for use in assays and purification of FIV. Applicant has determined a method by which sufficiently pure FIV antigen can be prepared in order to allow these monoclonal antibodies to be isolated, and to detect the presence of such monoclonal antibodies in a screening procedure. Applicant has also described means by which useful antibodies can be distinguished from those which are not useful in the invention.

Other features and advantages of the invention will be apparent from the following description of the preferred embodiments thereof, and from the claims.

DESCRIPTION OF THE PREFERRED EMBODIMENT

The drawings will first briefly be described

DRAWINGS

Figure 1:
Figure 2:
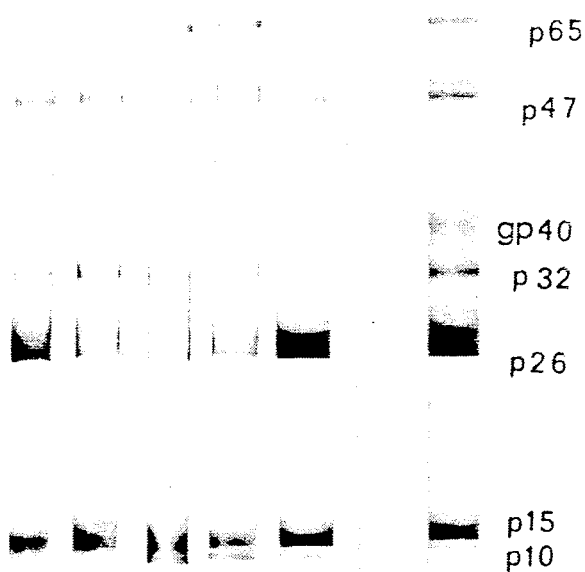

FIG. 1 is a photograph of the major viral associated proteins of FIV identified by polyacrylamide gel electrophoresis (PAGE) and stained with Coomassie Blue R250 (lane A); molecular weight standards are shown in lane B; and FIG. 2 is a photograph of a Western immunoblot analysis of antibodies to FIV found in serum from cats identified as positive by an ELISA assay for FIV antibodies;

FIV ANTIGEN

The FIV antigen is derived from FIV-infected cells, and takes the form of FIV virus particles, or is derived from FIV virus particles, as follows. (Synthetic antigens are also suitable in the assay, as are substantially purified polypeptides derived from FIV particles.) Master seed virus producing cultures were obtained in the form of a continuous feline cell line infected with FIV isolate #2427 (CRFK-FIV or Petaluma strain) from Dr. Niels Pedersen (University of California, Davis, Calif.). The parent cell line is Crandell feline kidney cell persistently infected with FIV. The cell line was deposited with the American Type Culture Collection on July 13, 1988 and assigned the number CRL9761. Applicants and their assignees acknowledge their responsibility to replace this culture should it die before the end of the term of a patent issued hereon, 5 years after the last request for a culture, or 30 years, whichever is the longer, and its responsibility to notify the depository of the issuance of such a patent, at which time the deposit will be made available to the public. Until that time the deposit will be made available to the Commissioner of Patents under the terms of 37 C.F.R. §1-14 and 35 U.S.C. §5112.

Other virus cultures can be obtained as described by Pedersen, supra, or by Harbour et al., 122 The Veterinary Record 84, 1988. Seed stocks of virus producing cell cultures were obtained by freeze-downs of FIV-infected master seed cell cultures following at least 19 post infection passages in culture. Additional seed stocks of virus producing cultures were obtained by either infection of the continuous feline cell culture with FIV master seed virus or by single cell microwell cloning of high level FIV producers from the original FIV infected master seed cell culture. For propagation, master seed virus infected feline cell cultures were inoculated into tissue cell culture flasks. Following growth to a confluent monolayer of cells, tissue culture fluid was harvested at intervals of 2-5 days.

Working seed virus was produced by propagation by the master seed cell line permanently infected with FIV. An inoculum was added to tissue culture flasks, in Dulbecco's Modified Eagles medium containing 2 mM L-glutamine and 4.5 g per liter/glucose (DME) containing 100 units per ml penicillin and streptomycin and 2 mM glutamine. An inoculum was added to tissue culture flasks, incubated, and the spent tissue culture fluid harvested when the cells were grown to confluence. The cells were released from the culture vessel with trypsin/EDTA and diluted between 1:5 and 1:25 (typically 1:8) in medium. Typically the flasks were incubated at 36° C.-38° C. for a maximum of 7 days (between 3 and 7 days) before fluid and cell harvest. The harvested fluid, including cell material, was centrifuged in a high speed centrifuge (Sorval RC-5B or Beckman J2-21) leading to separation of supernatant and cell pellet material The cell pellet was discarded, and the supernatant culture fluid used to prepare working virus. The clarified supernatant was made 0.5 M in NaCl and 4%-10% (usually 7%) in polyethylene glycol (PEG 8000, Sigma). Following overnight incubation at 2° C.-7° C., virus was pelleted (at 13,000×g for 30 min.) and resuspended in buffer (10 mM Tris, pH 7.6 300 mM NaCl, 1mM EDTA, at 2° C.-7° C.). After overnight incubation the virus was centrifuged at 13,000 ×g for 15 min., the pellet discarded and the supernatant centrifuged on a 50%/80% discontinuous glycerol step gradient in 10 mM Tris 300 mM NaCl, 1 mM EDTA at pH 7.6. Centrifugation was at 100,000×g for 3 hrs. at 4° C. and the FIV viral band at the 50%-80% interface collected. The band was suspended in 10 mM Tris, 0.3 M NaCl and 1 mM EDTA and diluted 1:3 in the buffer and repelleted at 100,000×g for 1 hr. The resulting pellet was purified virus and was resuspended in the above buffer and stored at −70° C. The resulting virus was substantially free from FIV host cell proteins and was composed of at least 5% p26 (the major nucleocapsid protein, as measured by densitometric scans of Coomassie Blue 250 stained SDS/PAGE as total protein). Such antigen is sufficiently pure for preparation of monoclonal antibodies and for screening for suitable monoclonal antibodies.

Such purified antigen may be obtained by other techniques, however, applicants have found that high molecular weight contaminants present in virus preparations may be eliminated by use of the high salt (i.e., greater than physiological range salt concentration) used in the gradient centrifugation procedure.

FIV GLYCOPROTEIN

In order to prepare monoclonal antibodies to viral glycoproteins, antigenic glycoprotein was firstly prepared as follows.

Actively growing CRFK FTLV infected cells were scraped from roller bottles, gently washed with phosphate-buffered saline (PBS), and pelleted. The cell pellet was gently resuspended in 10 mM sodium phosphate, pH 7.2, at a ratio of 1 ml buffer to 0.1 ml of cell pellet. This suspension was incubated on ice or refrigerated for 5-10 min., vigorously vortex mixed for 30 seconds, and four volumes of PBS with 1 mM PMSF added. The mixture was then vigorously homogenized for 90-120 seconds with a Brinkmann Homogenizer PT10/35 with a PTA 20 generator.

The resulting homogenate was clarified for 20 minutes at 5,000g. The supernatant fraction was discarded and the cell membrane pellet resuspended in PBS+0.2% Triton X-100 at a ratio of 2.5 ml buffer to 0.1 ml original cell pellet. The mixture was then vigorously homogenized for 90-120 seconds with a Brinkmann Homogenizer PT 10/35 with a PTA 20 generator The resulting homogenate was clarified at 100,000g for 1 hr, the supernatant decanted off and batch bound overnight at 20°-23° C. on Pharmacia Lentil Lectin Sepharose 4B at a ratio of 6 ml of resin to 5 ml of original cell pellet.

The Lentil Lectin Suspension was poured through a column, the resin collected, and washed with 15 column volumes of PBS+0.2% Triton X-100. The glycoproteins were then eluted from the resin by subjecting the resin to 5-10 column volumes of PBS+0.2% Triton X-100+200 mM methyl α-D mannopyranoside, collecting fractions of 1 column volume/tube.

The isolation of glycoproteins was verified by 9% SDS-PAGE electrophorisis, and checked using $^{35}$S-radiolabeled cell preparations in conjunction with RIPA data.

Further purification of viral glycoprotein from host cell glycoprotein includes use of the HPLC or use of a polyclonal antibody for affinity chromatography.

PREPARATION OF FIV MONOCLONAL ANTIBODIES

Balb/CJ (Jackson Labs) mice were immunized with an initial injection of 50 micrograms of FIV antigen per mouse mixed 1g:1 with Difco Bacto adjuvant complete After two weeks a booster injection of 100 micrograms of FIV antigen was injected into each mouse intravenously without adjuvant. Three days after the booster injection a fusion was performed with mouse myeloma cell lines FO or p3X63-Ag8.653. Mid log phase myeloma lines were harvested on the day of fusion and checked for viability. The cells were spun at 300×g for 8 min., separated from the growth medium, and resuspended in serum free DME.

For fusion, an FIV-inoculated mouse was killed by cervical dislocation and the spleen aseptically removed. The spleen was washed three times in serum free DME and placed in a sterile Petri dish containing 20 mls of complete medium (DME containing 20% bovine fetal serum, 100 units per ml of penicillin and streptomycin, and 1 mM sodium pyruvate) To release cells, the spleen was perfused with a 23 gauge needle.

Cells were placed in a 50 ml conical centrifuge tube and pelleted at 300×g for 8 min. The pellet resuspended in 5 ml of 0.17M ammonium chloride and placed on ice for 8 min. 5 ml of bovine fetal serum (20%) was added and the cells pelleted again at 300×g for 8 min. After resuspension in 10 ml DME the cells were counted and the spleen and myeloma cells mixed in a ratio of 3:1. The cell mixture was pelleted at 200×g for 10 minutes, the supernatant decanted, and the pellet allowed to stand for 5 min. Over a period of 1 min., 1 ml of 50% PEG (PEG 1500 mixed 1:1 with Hepes pH 8.1) at 37° C. was added. After 1 min. incubation at 37° C., 1 ml of DME was added over a period of another 1 min. and then a second 1 ml of serum free medium added over a period of 1 min. Finally, 10 mls of DME was added over ( a period of 2 min., the cells pelleted at 200×g for 8 min., and the pellet resuspended in complete medium containing 0.016 mM thymidine, 0.1 mM hypoxanthine, 0.5 micromolar aminopterin, and 10% hybridoma cloning factor (1×HAT). The cells were plated into 96-well plates.

After 3, 5 and 7 days half of the medium in the (-fusion plates was removed and replaced with fresh 1×HAT. After 11 days the hybridoma cell supernatant was screened by an ELISA test In this test, 96 well plates were coated with FIV antigen by standard technique. One hundred microliters of supernatant from each well was added to a corresponding well on a screening plate and incubated for 1 hr. at 20°-22° C. After incubation, each well was washed three times with distilled water and 100 microliters of a horseradish peroxide conjugate of goat anti-mouse IgG (H+L), A, M (1:1500 dilution) was added to each well and incubated for 1 hr. at 20°-22° C. After three washes with distilled water, the substrate OPD/hydrogen peroxidide was added and incubation continued for five to fifteen minutes. One hundred microliters of a stop solution (1 M hydrochloric acid) was then added and the absorbance at 490 nm read. Cultures which had an optical density reading greater than the control wells were removed to 2 $cm^2$ culture dishes, with the addition of normal mouse spleen cells in 1×HT medium. After a further three days all of the 2 $cm^2$ cultures were re-screened for antibody and those testing positive again were cloned by limiting dilution. The cells in each 2 $cm^2$ culture were counted and cell concentration adjusted to $1 \times 10^5$ cells per ml. The cells were diluted in complete medium and normal mouse spleen cells at concentrations of hybridoma cells of 5, 10 and 50 cells per ml added. The cells were plated into 96-well plates for each dilution. After 10 days the cloning plates were screened for growth. About 37% of all wells showed growth. The growth-positive wells were screened for antibody and those testing positive expanded to 2 $cm^2$ cultures and provided with normal mouse spleen cells. The cloning procedure was repeated 2 times until a stable antibody-producing hybridoma was obtained. At this point the cell culture was expanded from 2 to 9 to 75 to 150 $cm^2$ culture vessels, at which point ascite production could be commenced.

For ascites production, pristane primed IRCF1 female mice were used. 0.5 ml of pristane was injected intraperitoneally (IP) to each mouse, and the mouse allowed to rest for 10-60 days. At this time $4.5 \times 10^6$ cells were injected IP into each mouse and ascites formed in 7-14 days. Ascites fluid was harvested with a pasteur pipette through a hole in the peritoneum.

REACTIVITY OF MONOCLONAL ANTIBODIES

Monoclonals useful in this invention include those which are specific for FIV and form a sufficiently strong interation with an FIV epitope, and an FIV antigen, to be useful in an immunoassay, for example, an ELISA to detect FIV antigen. In order to determine which of the above monoclonal antibodies are useful in this invention two main tests were used. The first was to determine whether the monoclonal antibody can bind FIV antigen and be detected with a conjugate of polyclonal antibody to FIV (an ELISA test, described in detail below). The second test was to form a conjugate of the monoclonal antibody with horseradish peroxidase and then determine whether the monoclonal antibody was able to compete with itself for FIV antigen, and whether it would compete with other monoclonal antibodies for that antigen. The latter test is useful to determine which monoclonals are useful in a mixture of monoclonal antibodies; generally antibodies with different reactivities will be combined together to allow detection of a larger range of FIV antigens in a sample. Such combination will greatly increase sensitivity.

Another test is to perform a Western blot to determine whether the monoclonal antibody has good reactivity with one or more FIV antigens. Generally, those monoclonals which show poor reactivity, that is, produce faint bands on the Western blot, are not suitable in this invention. Yet another test involves radioimmunoprecipitation assay (RIPA) where FIV virus labeled with $^{35}S$-methionine is reacted with a monoclonal antibody to form within immunoprecipitate, and the immunoprecipitate run in a SDS-PAGE and autoradiographed to detect the labelled proteins. This analysis determines which- of the monoclonal antibodies is able to detect precursor FIV proteins and not just mature proteins.

Examples of such tests are presented below, along with a description of the identification of various FIV antigens (or proteins) by which the monoclonal antibodies can be distinguished. These examples are not limiting to this invention.

Referring to FIG. 1, proteins associated with purified FIV were analyzed by SDS/PAGE and compared with proteins isolated in an identical manner from the spent culture medium of uninfected cells. Analysis of the Coomassie Blue stained gels revealed three major proteins with molecular weights of about 10, 15, and 26 kD, named p10, p15 and p26, respectively.

When an ELISA test was performed using disrupted FIV to identify cats possessing polyclonal antibody to FIV proteins, and Western blot analysis then performed on feline sera determined to be positive by ELISA, each of the cats had antibodies which reacted with one or more proteins or antigens of molecular weight p10, 15, 26, 40 and 65 kD under the conditions used.

Referring to FIG. 2, a standard Western immuno blot was performed as described by Towbin et al., 76 Proc. Natl. Acad. Sci USA 4350, 1979. Briefly, FIV was disrupted with SDS and proteins transferred to a sheet of nitrocellulose. The nitrocellulose sheet was blocked with 30% calf serum, 1% bovine serum albumin (BSA), and 0.05% Tween 20 in Dulbecco s phosphate buffer saline. The sheets were cut into 0.5 cm strips and incubated with a 1:100 dilution of serum sample in blocking buffer for 2 hrs. for 20°-22° C. Strips were repeatedly washed with washing buffer (0.05% Tween 20 in Dulbecco's phosphate buffer saline) and then incubated with a second antibody (specific for feline heavy and light chain Ig) horseradish peroxidase conjugate (obtained from Kirkguard and Perry Laboratories Inc. Gaithersburg, MD). After 1 hr. incubation, the strips were repeatedly washed with washing buffer and incubated with the precipitating substrate 4-chloronaphthol for 10 min. The strips were partially dried and the results interpreted immediately. The serum in each of the lanes A-G was obtained from various cats infected with FIV. Predominant reactivity is detected with p. 26 and p15 and to a lesser extent with p10. Other proteins of 32, 40, 47 and 65 kD molecular weight are also detected.

Antibodies to glycoproteins can also be isolated. In particular, two glycoproteins of molecular weight 40 kD (gp40) and 130 kD p130 can be detected using PAGE and RIPA respectively. For example, an antibody 2F11) to envelope glycoproteins capable of recognizing antigenic sites possessed by the envelope precursor protein gp130 and the transmembrane protein gp40 was isolated as described below. Reactivity of this antibody with these proteins was determined by RIPA-PAGE analysis of $^{35}$S-methionine/cysteine labeled FIV-infected cell lysates. The 130 kD protein identified by the antibody was confirmed to be gp130 because it is sensitive to treatment with glycosidase H (which reduced the molecular weight of the glycoprotein to 75 kD). The 40 kD protein detected was resistant to treatment by this enzyme.

2F11 antibody was isolated using mice-Balb/C (Amitek) and disrupted whole virus (Staph A buffer 1:1 μg for half an hour at 20° C.-25° C.). 300 μg of the antigen was mixed 1:1 with Freund's complete adjuvant and 300 μg boosts given at 2 week intervals with no adjuvant. Fusion of the cells was performed at 5 weeks, after initial immunization, with 2-300 μg boosts. Mice were rested for 3 days before the fusion. The fusion partner was FO ATCC CRL 1646 (J. Immunol. Methods 35:1-21, 1980). The resulting antibody was screened on fusion plates, rescreened, subcloned, and the subclones expanded for ascite,production. The antibody is of subtype IgG$_1$ Kappa light chain.

Certain viral proteins, such as the gag (p26) antigens, are abundant in purified viral preparations, others such as the viral envelope proteins (gp130) tend to be lost during viral purification, and electrotransfer less efficiently for Western blot analysis than the gag antigens. Therefore, in order to more readily detect the viral envelope and the gag precurser proteins FIV cell extracts were labeled with $^{35}$S-methionine and cysteine and examined by immunoprecipitation (RIPA). Confluent cultures of cells infected with FIV were incubated for 30 min. in methionine and cysteine-free Dulbecco's modified Eagle's medium. The cell cultures were then incubated for 4 hrs. in 8 ml of the same medium containing 100 microCuries per ml of $^{35}$S-methionine and $^{35}$S-cysteine (specific activity 1200 Curies per mM, New England Nuclear Corporation, Boston, Mass.). The radioactive tissue culture fluids were removed and the cells lysed with 5 ml of 10 mM sodium phosphate buffer pH 7.5 containing 100 mM NaCl, 1% Triton×100, 0.5% sodium deoxycholate, 0.1% SDS, 0.1 mM phenylmethylsulfonylfluoride, and 100 Kallikren inactivator units of aprotenin per ml. (Sigma Chemical Co., St. Louis, Mo.). Before use, the cell lysates were clarified by centrifugation 100,000×g for 30 min. and the pellet discarded. Aliquots of the labelled cell lysates (0.1 ml) and 5 μl of serum being tested were mixed in a microcentrifuge tube and incubated for 1 hr. at 37° C. and then overnight at 4° C. The next day, 0.2 ml of a 5% suspension of protein A Sepharose CL-4B beads (Pharmacia, Piscataway, N.J.) in 10 mM of phosphate buffer, pH 7.5 containing 100 mM NaCl, 1% Triton X-100 and 0.1% SDS was added to each tube and mixed for 30 min. at 4° C. The antibody/antigen complexes bound to the protein A Sepharose beads were collected by centrifugation (2 min. at 20,000×g) and washed 3 times in lysing buffer The final pellet was resuspended in 25 μl SDS/PAGE loading buffer and heated and 100° C. for 3 minutes. The Sepharose beads were removed by centrifugation and the supernatant applied to a PAGE. Gels were processed for fluorography using enlightening TM (New England Nuclear Corporation, Boston, Mass.) and exposed at −70° to Kodak XR-5 film. Sera from experimentally infected cats recognize proteins of 15, 22, 36, 40, 47, 110 and 130 kD. Although there were some quantitative and qualititative differences all cats appear to mount a response to p22, gp40, gp47 and gp130.

In order to determine which of the proteins identified by RIPA-PAGE analysis were related to the major internal structural protein, p26, RIPA-PAGE analysis was carried out using monoclonal antibodies which reacted with p26 as determined by Western blotting. This monoclonal immunoprecipitated proteins p47, p36, p22 and p15. High molecular weight proteins (130 kD) of FIV which were not detected by the p26 specific monoclonal antibody. A protein of molecular weight 100 kD was also detectable utilizing serum antibodies obtained from some infected cats.

The monoclonals isolated as described above and tested by the above techniques were found to react specifically with p10, p15, p26, p47 and to belong to the subtypes IgM, IgG1, IgG2, IgG3, IgG2A, and IgG2B. Of these, some monoclonals reacted poorly with p26 and p47 and others reacted strongly or at an intermediate level. We found that the most significant test for usefulness of any specific antibody was the ELISA test In a specific test, microtiter plates were coated with the anti-FIV monoclonal antibodies at 1 microgram per well in coating buffer (0.1 M NaHPO$_4$ pH 7.2). The monoclonal antibodies were incubated at 3° C. overnight. The plates were then washed two times with phosphate buffered saline and 0.05% Tween-20 and the remaining liquid aspirated The wells were then blocked with 1% bovine serum albumin in 0.1 M Tris pH 7 and this wash solution aspirated. FIV sample or a known FIV-antigen was then added by standard procedure. Horseradish peroxidase conjugate was prepared using either purified oat anti-FIV IgG or a second anti-FIV monoclonal antibody. Conjugate was then provided to the test wells. Following washing, a substrate-chromogen mixture (TMB/H$_2$O$_2$) was added to test wells and incubated for 15 minutes. Optical densities of wells at 650 nm was then determined. In this test a normal negative gave a result of approximately 0.06 O.D. units. A poor monoclonal antibody provided with 1 μg/ml of FIV antigen gave an O.D. reading of less than 0.5, cultures having a fairly good antibody yielded O.D. readings of 0.5 to 1.0. A good monoclonal antibody typically yielded an O.D. of greater than 0.2 when 1 ng per ml FIV was provided.

In a second experiment, each of the monoclonal antibodies was conjugated with horseradish peroxidase and analyzed in a competition assay for FIV antigen. In this way it was determined which monoclonal antibodies could be used in mixtures for standard immunoassays for FIV. Particularly good. mixtures included the mixture of 2D4 or 3H8 (specific for p26), 4F2 (specific for p15, p26 and p50) and 6E6 (specific for p26 and p50).

DEPOSITS

Cell lines producing monoclonal antibodies 3H8, 4F2 and 6E6 were deposited with ATCC on Nov. 1, 1988 and given designation numbers HB9888, HB9889 and HB9890, respectively. The cell line producing monoclonal antibody 2F11 was deposited with the ATCC on Nov. 7, 1989 and given designation number HB10295.

Applicants assignee, Idexx Corp., acknowledges its responsibility to replace these cultures should they die before the end of the term of a patent issued hereon, 5 years after the last request for a culture, or 30 years, whichever is the longer, and its responsibility to notify the depository of the issuance of such a patent, at which time the deposits will be irrevocably made available to the public. Until that time the deposits will be made available to the Commissioner of Patents under the terms of 37 CFR §1–14 and 35 USC §112.

Other embodiments are within the following claims.

We claim:

1. A monoclonal antibody specific for an epitope of the feline immunodeficiency virus-encoded (FIV-encoded) antigenic protein p15.

2. A monoclonal antibody specific for an epitope of the FIV-encoded antigenic protein p. 26.

3. A monoclonal antibody specific for an epitope of the FIV-encoded antigenic protein gp40.

4. The monoclonal antibody of any of claims 1–3, wherein said antibody has sufficient affinity for said epitope to selectively identify said epitope in an immunoassay for FIV.

5. The monoclonal antibody of any of claims 1–3, said antibody recognizing an epitope on an FIV particle.

6. The monoclonal antibody of any of claims 1–3, conjugated with a detectable label.

7. The monoclonal antibody of claim 6, said label being an enzyme.

8. The monoclonal antibody of claim 7, said enzyme being horseradish peroxidase.

9. A monoclonal antibody produced from the cell line deposited as ATCC number HB9888.

10. A monoclonal antibody produced from the cell line deposited as ATCC number HB9889.

11. A monoclonal antibody produced from the cell line deposited as ATCC number HB9890.

* * * * *